(12) United States Patent
Nobel et al.

(10) Patent No.: US 6,618,173 B1
(45) Date of Patent: Sep. 9, 2003

(54) METHOD FOR AUTOMATIC PREVENTION OF VERTICAL STREAKS BY SELECTIVELY APPLYING GAINS TO THE OUTPUT SIGNALS OF OPTICAL SENSOR ELEMENTS

(75) Inventors: Gary M. Nobel, Poway, CA (US); Daniel Wee, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 09/414,023

(22) Filed: Oct. 7, 1999

(51) Int. Cl.[7] .............................. H04N 1/46; H04N 1/40; H04N 1/04; H01L 27/00; G06K 9/40
(52) U.S. Cl. ...................... 358/513; 358/533; 358/445; 358/446; 358/447; 358/483; 250/208.1; 382/274; 382/275; 382/254
(58) Field of Search ................. 358/513, 533, 358/445, 446, 447, 483; 250/208.1; 382/274, 275, 254

(56) References Cited

U.S. PATENT DOCUMENTS 5,771,107 A * 6/1998 Fujimoto et al. ........... 358/453
5,798,847 A * 8/1998 Aerts ......................... 358/464
6,195,161 B1 * 2/2001 Edgar ........................ 250/330
6,295,383 B1 * 9/2001 Smitt et al. ................. 358/461

\* cited by examiner

*Primary Examiner*—Edward Coles
*Assistant Examiner*—Houshang Safaipour

(57) ABSTRACT

A method for automatic prevention of vertical streaks involves processing output signals from a plurality of photosites to determine what gain is appropriate for each output signal. An exemplary preferred method distinguishes between different types of output signals for which a first type of gain is appropriate and other output signals for which a second type of gain is appropriate. The first type of gain is a proportionate gain. The second type of gain is determined from at least one gain which is appropriate for output signals generated by neighbor photosites. The second type of gain is applied to the output signals when the processing indicates that a light-absorbing optical obstruction associated with the photosites generating the output signals appears to be positioned in an optical path of the photosites on or between a scan surface area over which an object to be imaged by the photosites is positioned and a calibration strip facing the scan area surface.

24 Claims, 8 Drawing Sheets

METHOD FOR AUTOMATIC PREVENTION OF VERTICAL STREAKS BY SELECTIVELY APPLYING GAINS TO THE OUTPUT SIGNALS OF OPTICAL SENSOR ELEMENTS

CROSS-REFERENCE TO RELATED APPLICATIONS

This application is related to U.S. patent application Ser. No. 09/414,391 entitled "Method For Automatic Removal Of Vertical Streaks By Modifying Image Data Associated With Non-Homogenous Image Elements" filed herewith.

BACKGROUND OF THE INVENTION

1. Field of Invention

The present invention relates generally to a method for automatic prevention of vertical streaks and, more specifically, to a method for automatic prevention of vertical streaks by selectively applying gains to the output signals of optical sensor elements.

2. Description of the Related Art

Scanners typically include an array of optical sensor elements and a scan area (e.g., plate of glass) where an object to be imaged by the sensor elements is positioned. An optical path including, for example, lens and mirrors, spans between the sensor elements and the scan area.

Referring to FIG. 2, a subsystem 200 of a typical scanner includes an optical sensor device 202, a lens 204, a transparent plate 206 and a calibration strip 208. The transparent plate 206 includes a scan area surface 210 over which an object 212 to be scanned is positioned. An exemplary calibration strip 208 spans across the entire scan area surface 210 and is formed from plastic with a uniform exterior color such as white.

The optical sensor device 202 is typically a linear array of optical sensor elements or photosites which convert optical images to electrical output signals. An exemplary optical sensor device 202 comprises a 2,700-bit×3CCD (Charge Coupled Device) color linear image sensor such as the NEC µPD3720 integrated circuit which has a color filter that provides primary colors (red, green and blue) via rows of photosites 214, 216 and 218, respectively, which are arranged on the sensor device 202 as shown.

A problem with the subsystem 200 is that different photosites, due to manufacturing imperfections, do not necessarily generate the same output signal when imaging identical objects. Another problem with the subsystem 200 If is that the optical path 220 (shown unfolded) between the optical sensor device 202 and the object 212 introduces inconsistencies in the output signals because the photosites at the end portions 222 and 224 of the optical sensor device 202 receive lower levels of light from an object 212 of uniform color than the photosites near the center portion 226 of the optical sensor device 202. Therefore, in order to achieve uniformity in the levels of the output signals across the optical sensor device 202, some form of compensation or calibration of the output signals is necessary. To this end, the subsystem 200 includes the calibration strip 208 which is used to calibrate the output signals of the optical sensor device 202.

Referring to FIG. 3, a functional block diagram 300 shows that output signals 302 generated by the optical sensors 202 are provided with pixel-by-pixel gain 304 to generate calibrated output signals 304. During the calibration process, the photosites of the optical sensor device 202 image the uniformly colored calibration strip 208 before the object 212 to be scanned is positioned on the scan area surface 210. Each photosite in the scanner is "queried" to determine how much light it "sees". Across the optical sensor device 202, from the left end 222 to the right end 224, the output signals 302 appear, for example, as shown in FIG. 4. In order to achieve uniformity in the levels of the output signals across the optical sensor device 202, a "proportionate" pixel-by-pixel gain 304 as shown in FIG. 5 is applied to the output signals 302. The term "proportionate" means an inversion or other appropriate function of the output signals 302 such that the calibrated output signals 304 appear as the uniform output level shown in FIG. 6. By way of example, suppose an average photosite reports a value of 100. If one photosite reports a lower value—say 50—then the amplification for that one photosite will be set twice as high as the amplification for the average photosite. After the calibration process is completed, the pixel-by-pixel gain 304 is saved, for example, in firmware of the scanner, and applied during subsequent scanning. Thus, the net signal from the photosite and its amplification are the same for all photosite-amplification pairs.

Even though each photosite gets a "customized" amplification, unfortunately, this does not accommodate a situation where an optical obstruction is positioned between the calibration strip 208 and the scan area surface 210 during the calibration process. The term "optical obstruction" means an object which has any effect on light transmitted therethrough. Optical obstructions include, but are not limited to, paper dust, plastic dust, skin particles, metal particles and glass particles.

Referring again to FIG. 2, the subsystem 200 is shown with optical obstructions "A", "B", "C" and "D" positioned between the optical sensor device 202 and the calibration strip 208. More specifically, the optical obstructions "A", "B", "C" and "D" are positioned, respectively, on the scan area surface 210, in the optical path 220, in the optical path 220 sufficiently near the scan area surface 210 to be illuminated by a light source (not shown), and on the optical sensor device 202. The optical obstructions "A", "B" and "D" are dark debris which are light-absorbing, i.e., tending to absorb light. The optical obstruction "C" is reflective. During the calibration process, when these optical obstructions are present, the output signals 302, from the left end 222 to the right end 224 of the optical sensor device 202, appear, for example, as shown in FIG. 7. In order to achieve uniformity in the levels of the output signals across the optical sensor device 202, a "proportionate" pixel-by-pixel gain 304 as shown in FIG. 8 is applied to the output signals 302. As shown in FIG. 9, a uniform photosite output signal level with proportionate gain applied is the result of the calibration process. However, if the optical obstruction "A" is displaced from the optical path 220, for example, by an object 212 moving across the scan area surface 210, the calibrated output signal levels will then appear as shown in FIG. 10 with a large spike corresponding to the photosite that was imaging the optical obstruction "A" during the calibration process. As a result, during scanning, this erroneously high gain causes all scan data from that photosite to have a higher signal than it should. The net effect is that there is a bright vertical line in the scan, copy or fax output which runs the entire length of the image.

One possible approach to solving the problem described above would be to move the optical sensor device 202 relative to the calibration strip 208 during the calibration process. A disadvantage of such an approach is that it adds to the complexity of the scanner and makes it more expensive by requiring a mechanism for moving either the optical sensor device 202 or the calibration strip 208 relative to the other.

Thus, a need exists for a method for eliminating vertical streaks in scan data caused by optical obstructions in the optical path of the scanner. Also, a need exists for a method for "intelligently" determining when the signal from a photosite is truly low and needs to be compensated for with a large amplification and when a photosite is low due to dust which is likely to be dislodged from the optical path by the object being scanned and, therefore, needs to have an "ordinary" amplification.

SUMMARY OF THE INVENTION

A method for automatic prevention of vertical streaks in accordance with one embodiment of the present invention includes the steps of: processing output signals from an optical sensor; and selectively applying gains to the output signals depending upon differences between each output signal and its respective neighbor output signals.

In a preferred embodiment, the step of applying gains further includes identifying output signals to which a proportionate gain is to be applied and output signals to which a gain which is appropriate for at least one of the neighbor output signals is to be applied. Output signals to which proportionate gains are to be applied include: an output signal for which the difference between the output signal and its neighbor output signals indicates that an optical obstruction is not likely to be present in an optical path associated with the output signal; an output signal for which the difference between the output signal and its neighbor output signals indicates that a reflective particle is likely to be present in an optical path associated with the output signal; and an output signal for which the difference between the output signal and its neighbor output signals indicates that an optical obstruction is likely to be positioned in an optical path associated with the output signal between the optical sensor and a scan area surface over which an object to be imaged by the optical sensor is positioned. Output signals to which gains appropriate for at least one of the neighbor output signals are to be applied include an output signal for which the difference between the output signal and its neighbor output signals indicates that an optical obstruction is likely to be positioned in an optical path associated with the output signal on or between the scan surface area and a calibration strip facing the scan area surface.

A method for automatic prevention of vertical streaks in accordance with another embodiment of the present invention includes the steps of: receiving output signals from a plurality of optical sensor elements; and for each of the sensor elements, comparing the value of the output signal with the values of the output signals of neighbor sensor elements to determine whether an optical obstruction appears to be present in an optical path associated with any of the sensor elements. In a preferred embodiment, the optical sensor elements are configured as an array, and the method also includes the steps of: distinguishing between narrow dips and wide dips in magnitudes of the output signals moving linearly across the array; and applying gains to the output signals depending upon whether the dips are narrow or wide.

A method for automatic prevention of vertical streaks in accordance with another embodiment of the present invention includes the steps of: identifying an element of an optical sensor for which a particle appears to be positioned in an optical path of the element between a scan surface area over which an object to be imaged by the optical sensor is positioned and a calibration strip facing the scan area surface; and applying a gain to an output signal generated by the element, the gain being appropriate for at least one other element of the optical sensor.

The above described and many other features and attendant advantages of the present invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings.

DETAILED DESCRIPTION OF THE PREFERRED EMBODIMENTS

The following is a detailed description of the best presently known mode of carrying out the invention. This description is not to be taken in a limiting sense, but is made merely for the purpose of illustrating the general principles of the invention.

Figure 1:
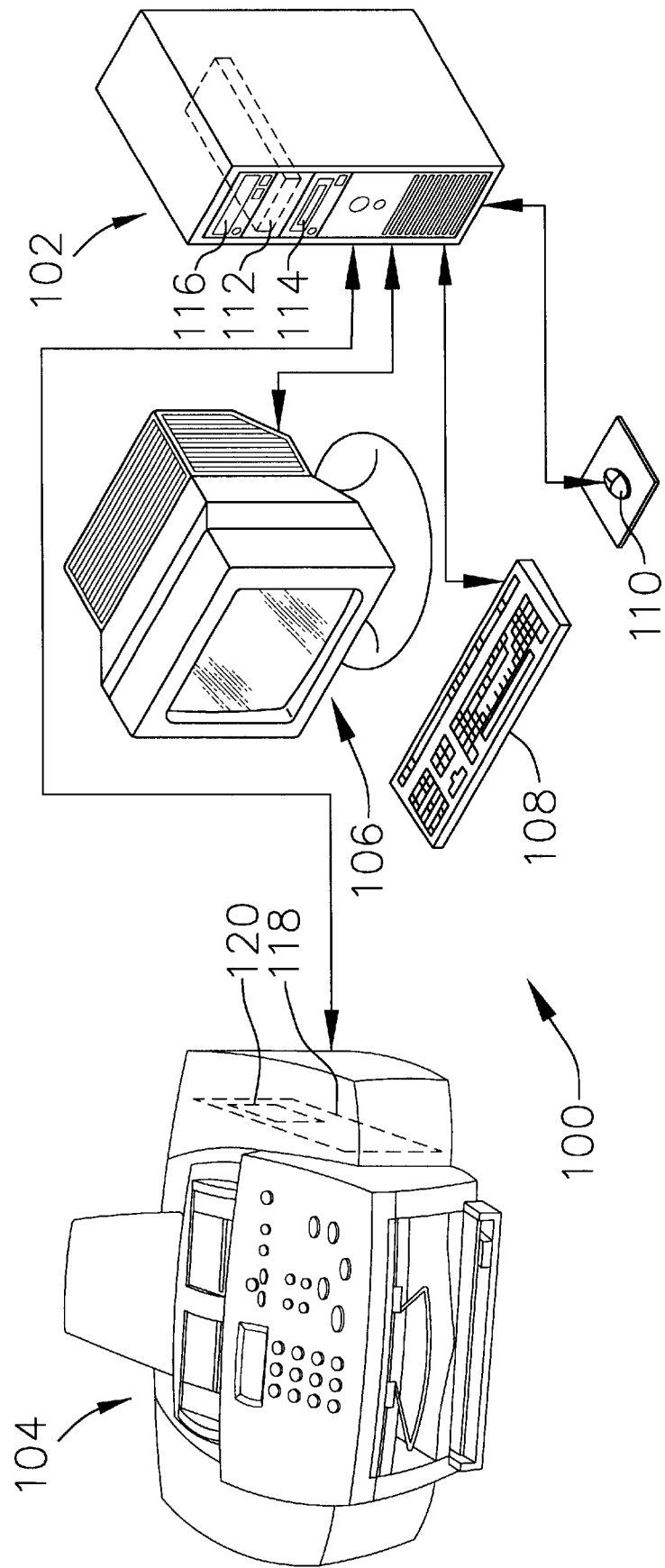
FIG. 1 is a perspective view of a system including a personal computer and a sheet fed scanner, the system being configured to employ the principals of the present invention.

FIG. 1 shows a system 100 configured to employ the principals of the present invention. The system 100 includes a computer 102, scanner 104, monitor 106 and various user-input devices such as a keyboard 108 and a mouse 110 functionally interconnected as shown. The computer 102 comprises, for example, a personal computer ("PC") with a hard drive 112 (shown in phantom lines), a disk drive 114 and a CD-ROM drive 116. An exemplary preferred scanner 104 comprises an "All-In-One" product such as the HP OfficeJet T Series (T45/65) which provides integrated printing, faxing, scanning and copying functions, all in color. The scanner 104 includes a circuit card 118 with firmware 120 (both shown in phantom lines).

According to the present invention, algorithms employed by an exemplary preferred method for automatic prevention of vertical streaks are stored in the firmware 120. It should be understood, however, that the scope of the present invention includes other computational and data storage configurations.

Generally, the method for automatic prevention of vertical streaks processes output signals from a plurality of photosites to determine what gain is appropriate for each output signal. More specifically, the method for automatic prevention of vertical streaks provides a means for distinguishing between output signals for which a first type of gain is appropriate and other output signals for which a second type of gain is appropriate. The first type of gain is a proportionate gain which is applied to the output signals in most circumstances. The second type of gain is determined from at least one gain which is appropriate for output signals generated by neighbor photosites. The second type of gain is applied to the output signals when the processing reveals that an optical obstruction associated with the photosites generating the output signals appears to be positioned in an optical path of the photosites between a scan surface area over which an object to be imaged by the photosites is positioned and a calibration strip facing the scan area surface, or on the scan surface area or on the calibration strip.

Figure 11A:
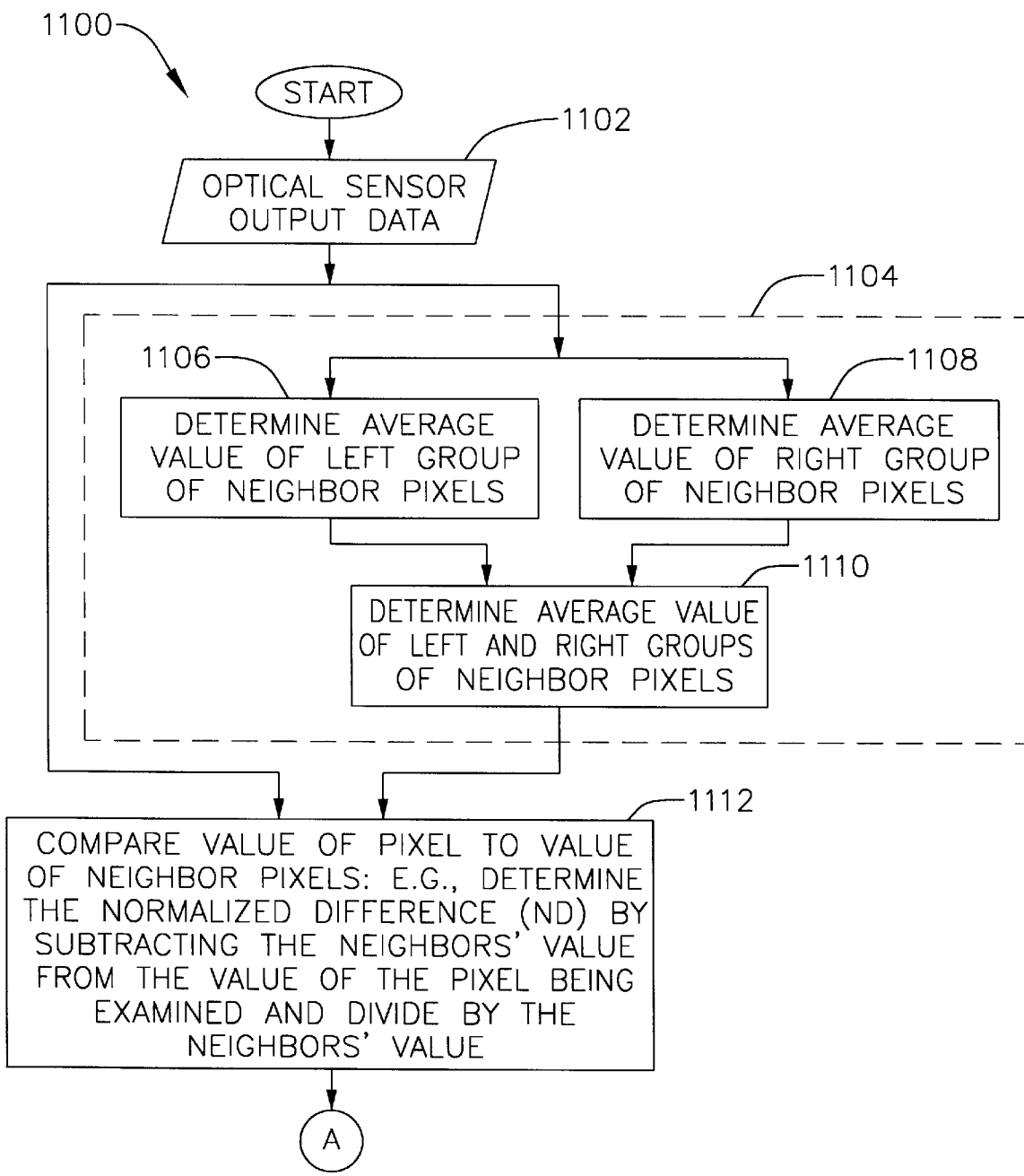
FIGS. 11A–11C are a flowchart showing a method for automatic prevention of vertical streaks according to an exemplary preferred embodiment of the present invention.
Figure 11B:
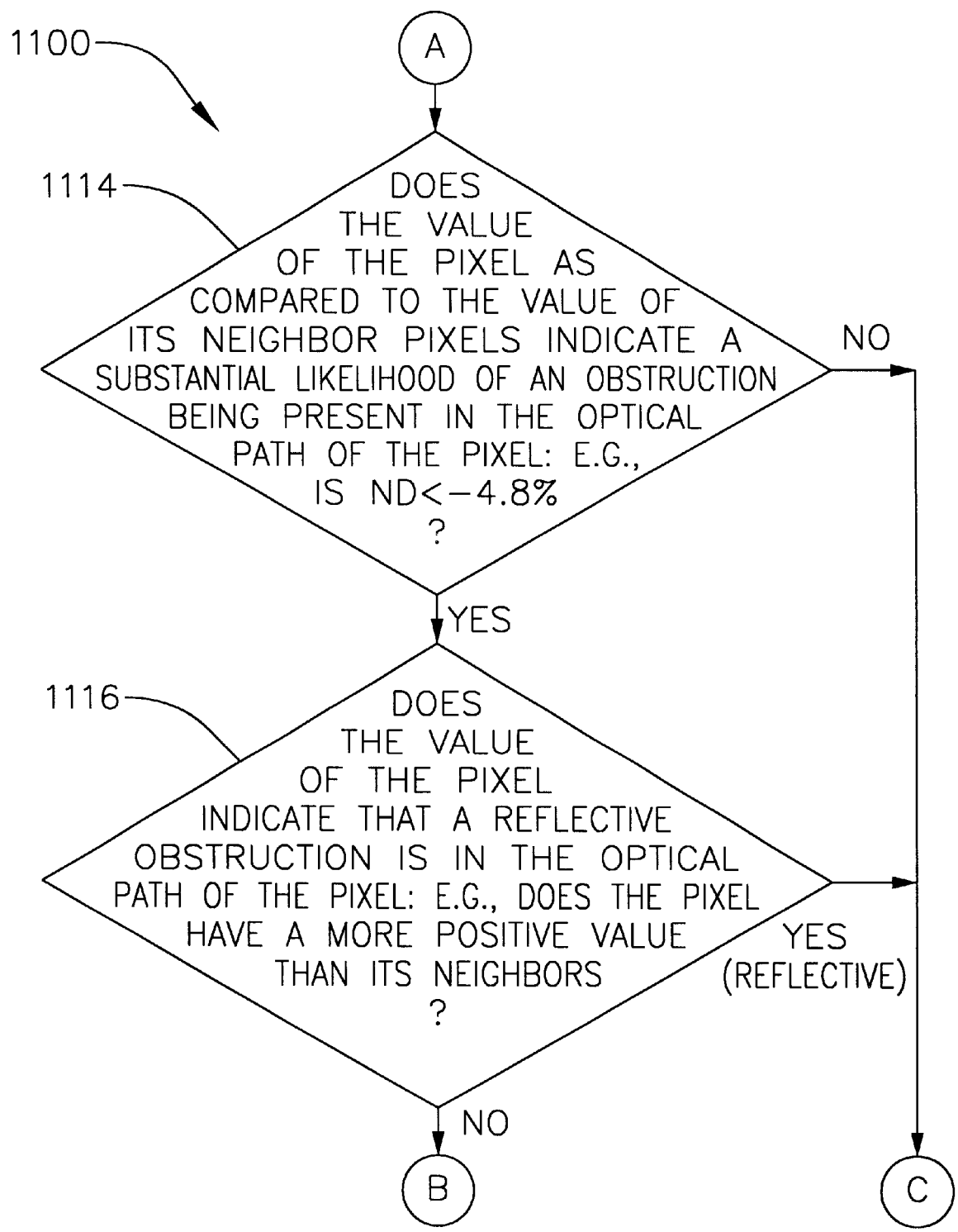
Figure 11C:
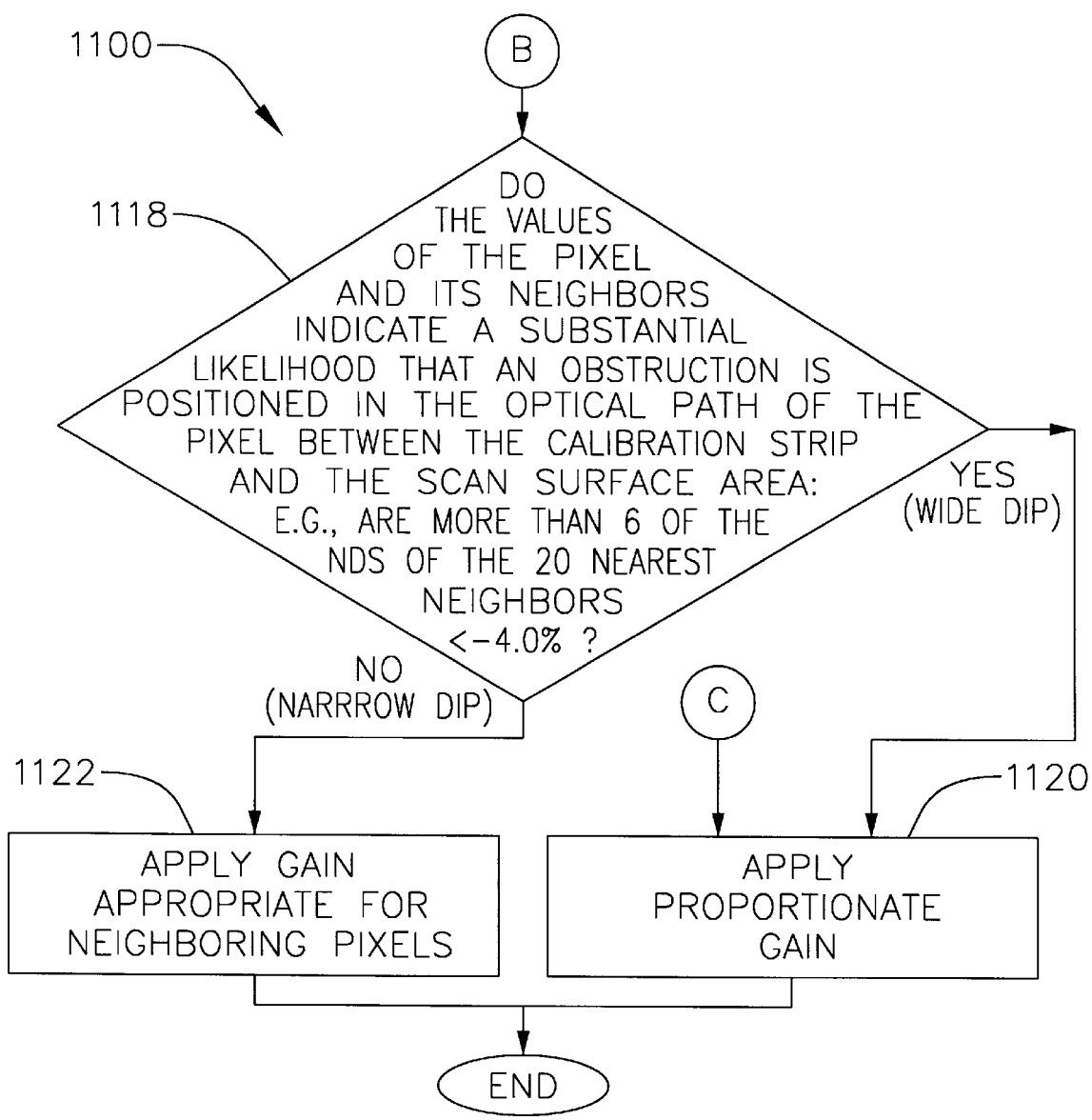

FIGS. 11A–11C show the steps of an exemplary preferred "debris prevention processing" method 1100 according to the present invention. As discussed supra, the computational features, algorithms, etc. of the "debris prevention processing" method 1100 are embodied in the firmware 120 which receives optical sensor output data 1102 corresponding to the optical sensor output signals 302.

According to the exemplary preferred method 1100, the optical sensor output data 1102 is next processed at executable block 1104 to determine the values of neighbor pixels for a pixel under consideration. In the following discussion, the term "pixel" refers to the portion of an image generated from an output signal 302 of the optical sensor device 202. However, it should be understood that the present invention is not limited to an imaging arrangement where there is a one-to-one relationship between the pixels (or other image elements) and the photosites of the optical sensor device 202.

Figure 2:
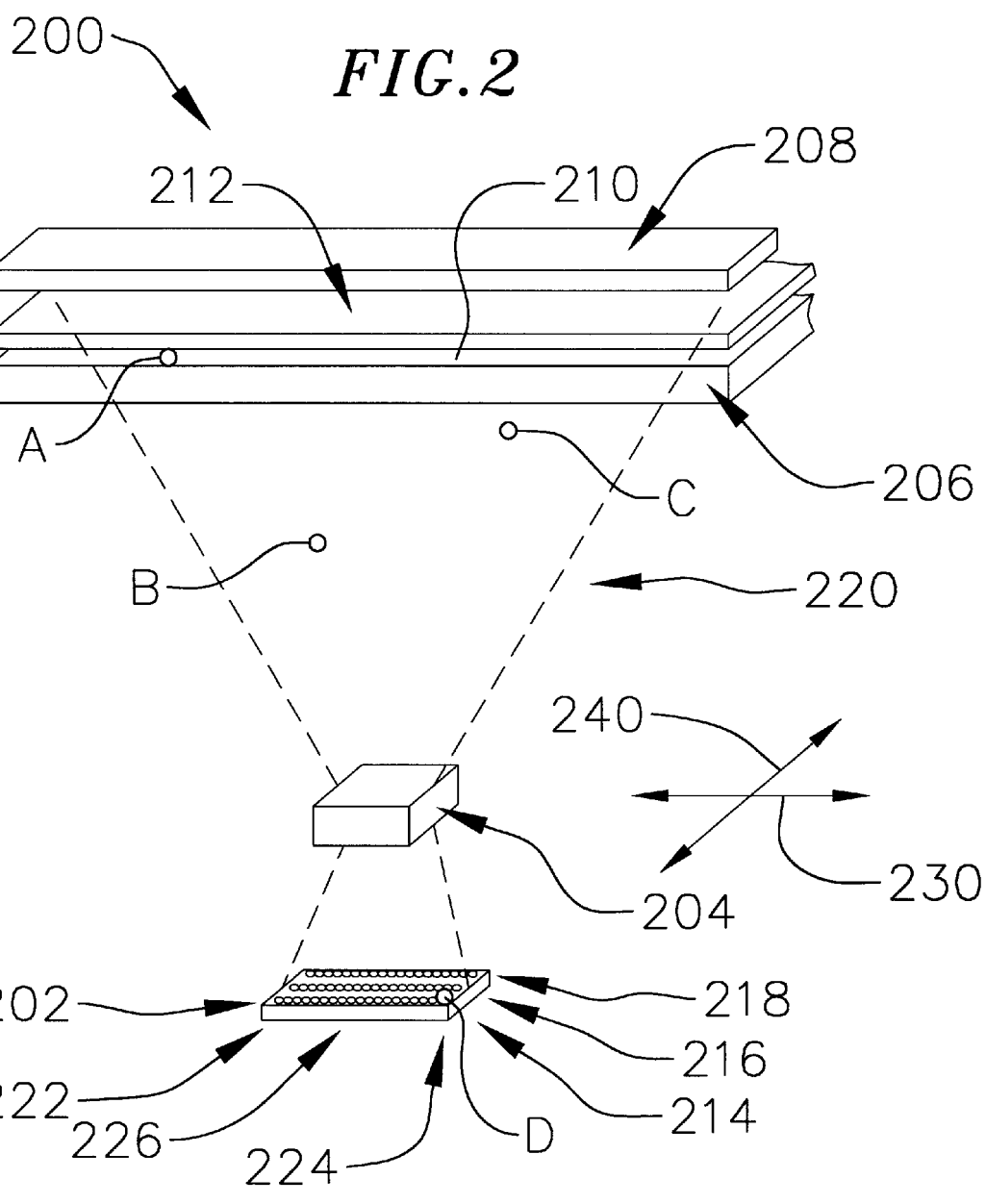
FIG. 2 is a partial perspective view of an array of optical sensors of the scanner of FIG. 1 and its unfolded optical path.
Figure 3:
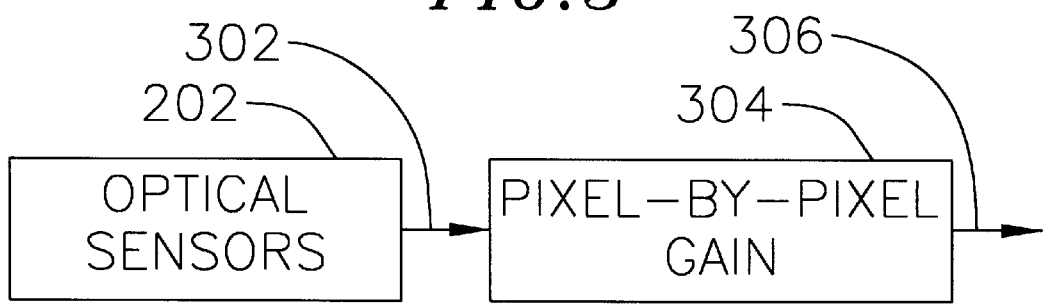
FIG. 3 is a functional block diagram showing a pixel-by-pixel gain applied to an output of the optical sensors of FIG. 2 according to an exemplary preferred embodiment of the present invention.
Figure 4:
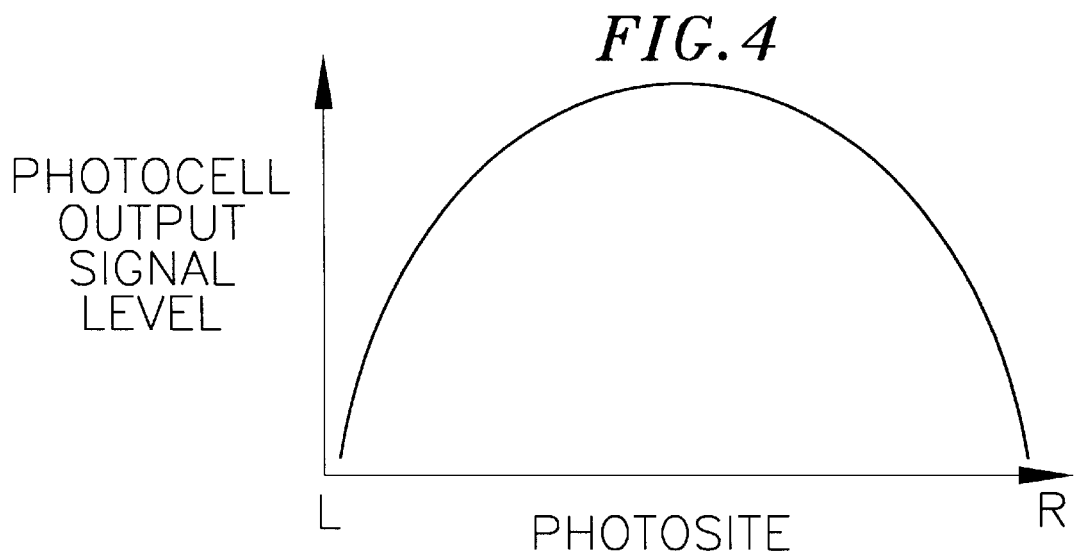
FIG. 4 is a graph of photosite output signal levels when the optical sensors of FIG. 2 are imaging an object of uniform color, such as a calibration strip, through the optical path.
Figure 5:
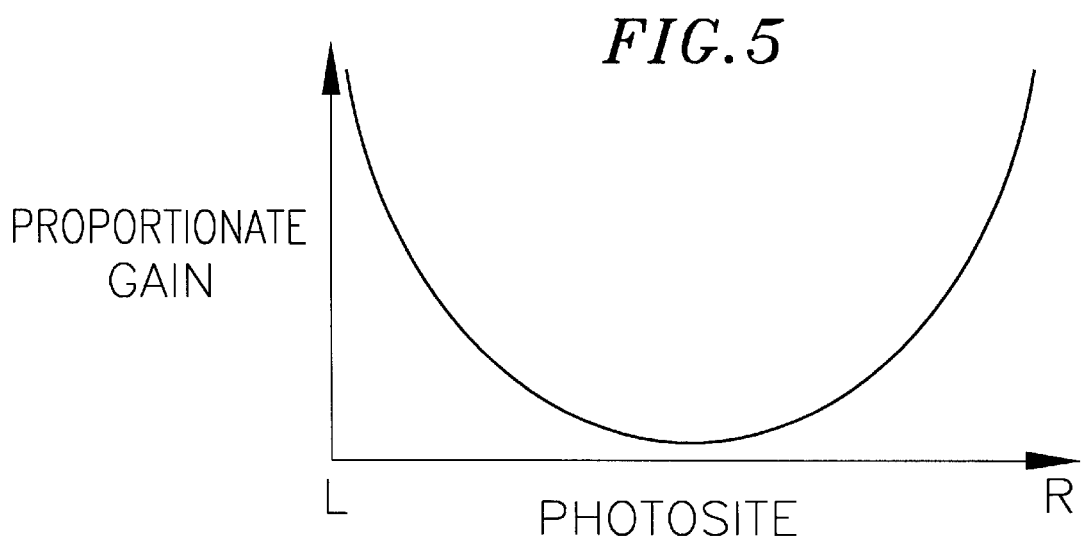
FIG. 5 is a graph of proportionate gain values calculated for the photosite output signal levels of FIG. 4.
Figure 6:
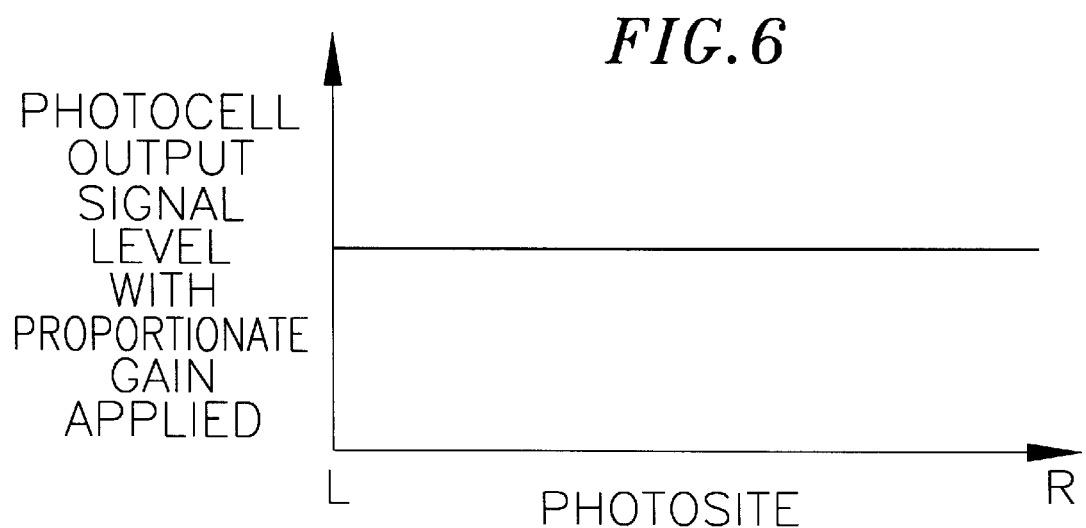
FIG. 6 is a graph of the photosite output signal levels of FIG. 4 with the proportionate gains of FIG. 5 applied.
Figure 7:
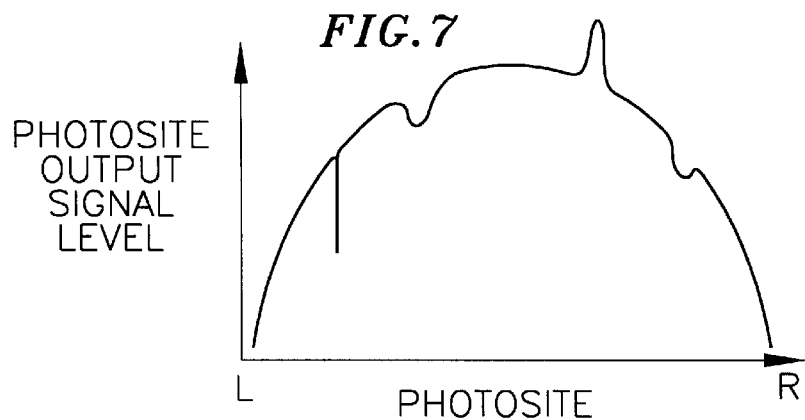
FIG. 7 is a graph of photosite output signal levels when the optical sensors of FIG. 2 are imaging an object of uniform color, such as a calibration strip, through the optical path, with the obstructions denoted as "A", "B", "C" and "D" positioned in the optical path as shown in FIG. 2.
Figure 8:
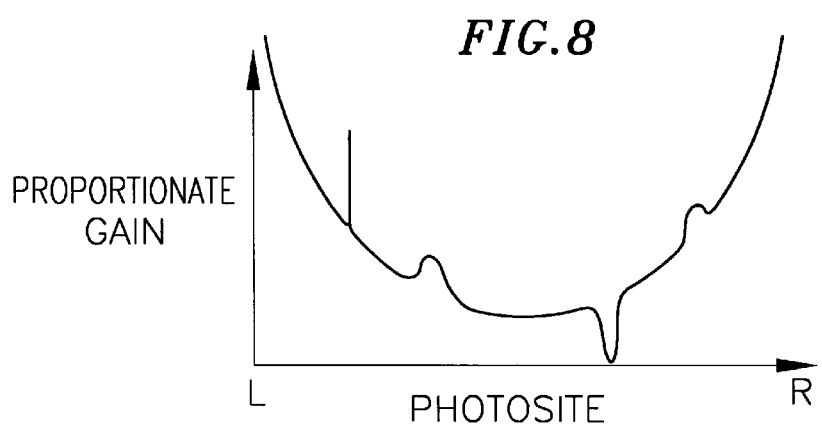
FIG. 8 is a graph of proportionate gain values calculated for the photosite output signal levels of FIG. 7.
Figure 9:
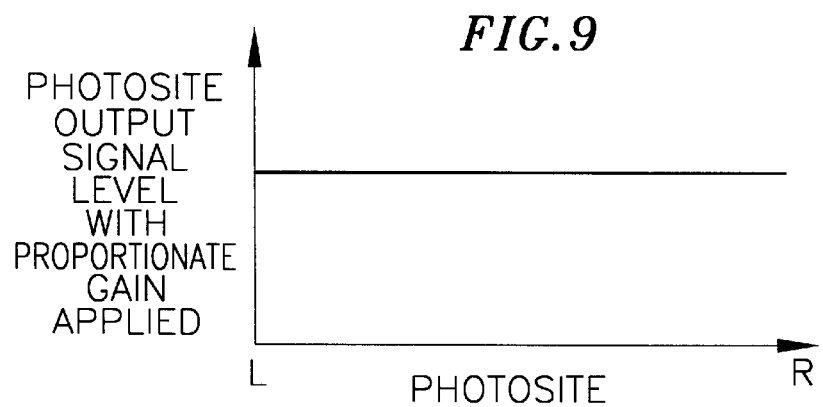
FIG. 9 is a graph of the photosite output signal levels of FIG. 7 with the proportionate gains of FIG. 8 applied.
Figure 10:
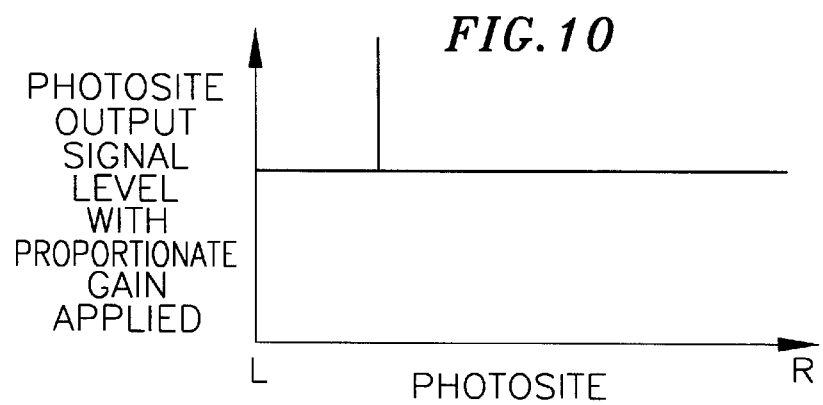
FIG. 10 is a graph of the photosite output signal levels of FIG. 7 with the proportionate gains of FIG. 8 applied after the "A" obstruction shown in FIG. 2 has been removed from the optical path.
Figure 12:
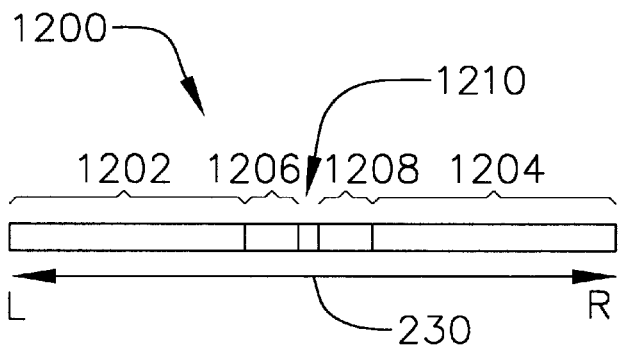
FIG. 12 illustrates a spatial relationship between a pixel under consideration, according to the method of FIGS. 11A–11C, and its neighboring pixels.

Referring to FIG. 2, the output signals 302 of the optical sensor device 202 along a "fast scan" axis 230 are processed to determine the values of the neighbor pixels for a pixel under consideration. FIG. 12 shows a group of pixels 1200 which correspond to a group of photosites along the "fast scan" axis 230.

Referring to FIG. 11A, the processing step 1104 more specifically pertains to determining the values of neighbor pixels which are within a known range of distances from the pixel under consideration. In an exemplary preferred processing step 1104, the optical sensor output data 1102 for these output signals 302 are processed according to steps 1106, 1108 and 1110. In step 1106, an average value of a left group of pixels 1202 (FIG. 12) is determined. In step 1108, an average value of a right group of pixels 1204 (FIG. 12) is determined. In step 1110, an average value of the left and right groups of pixels 1202, 1204 is determined. In an exemplary preferred processing step 1104, the left group of pixels 1202 comprises the pixels from 4 to 15 pixels to the left of a pixel 1210 (FIG. 12) being examined, and the right group of pixels 1204 comprises the pixels from 4 to 15 pixels to the right of the pixel 1210 being examined. Therefore, in an exemplary preferred processing step 1104, pixels adjacent the pixel under consideration are skipped.

Referring to FIG. 12, a left group of skipped pixels 1206 is positioned between the left group of pixels 1202 and the pixel 1210 under consideration. In a symmetrical fashion, a right group of pixels 1208 is positioned between the right group of pixels 1204 and the pixel 1210 under consideration. In an exemplary preferred processing step 1104, the left and right groups of skipped pixels 1206, 1208 comprise the 3 pixels to the left and right of the pixel 1210, respectively, thus providing a "skip distance" of 6 pixels. Since the typical optical obstruction (e.g., piece of dust) is 4/100 inches across and the distance between adjacent photosites in a particular row of photosites is 1/300 inches, approximately 90% of the optical obstructions are 4 pixels wide or less. Thus, it has been observed that a skip distance of 6 pixels is appropriate for determining values of neighbor pixels for the purposes of the present invention. However, it should be understood that adjustments to the numbers of pixels in the pixel groups 1202, 1204, 1206 and 1208 are also contemplated as being within the scope of the present invention. For example, adjustments can be made to accommodate different optics 204 in the optical path 220 and depending upon the particular application.

Referring again to FIG. 11A, the exemplary preferred method 1100 next involves a processing step 1112 which generally involves a comparison between the value of the pixel 1210 under consideration and the average value of its neighbor pixels as determined in step 1104. In an exemplary preferred step 1112, this comparison is made by calculating the normalized difference (ND) of the value of the pixel 1210 under consideration and the average value of its neighbor pixels as follows:

$$ND = \left[\frac{(ValueofPixelUnderConsideration) - (Avg.NeighborPixels'Value)}{(Avg.NeighborPixels'Value)}\right]$$

Turning to FIG. 11B, the next step of the exemplary preferred method 1100 is decisional diamond 1114. At this step in the processing, it is determined whether the value of the pixel under consideration as compared to its neighbor pixels indicates a substantial likelihood of an optical obstruction being present in the optical path of the pixel under consideration. In an exemplary preferred step 1114, the answer to this question is "yes" if the normalized difference (ND) calculated in step 1112 is less than an empirically determined threshold, e.g., −4.8%. If the answer to this question is "yes", the processing advances to step 1116 (discussed below). If the answer to this question is "no", the processing advances to executable block 1120 (FIG. 11C) where a proportionate gain calculated as discussed previously is applied to the pixel under consideration.

Figure 13:
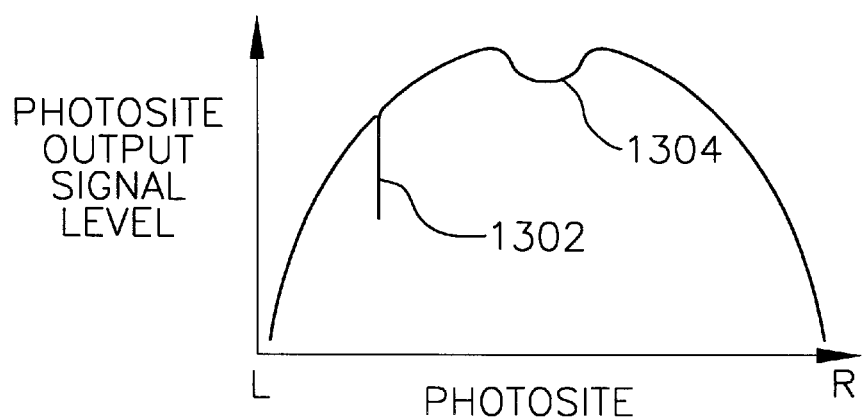
FIG. 13 is a graph of photosite output signal levels of the optical sensors of FIG. 2, the graph shows a narrow dip and a wide dip in the output signal levels caused by optical obstructions.
Figure 14:
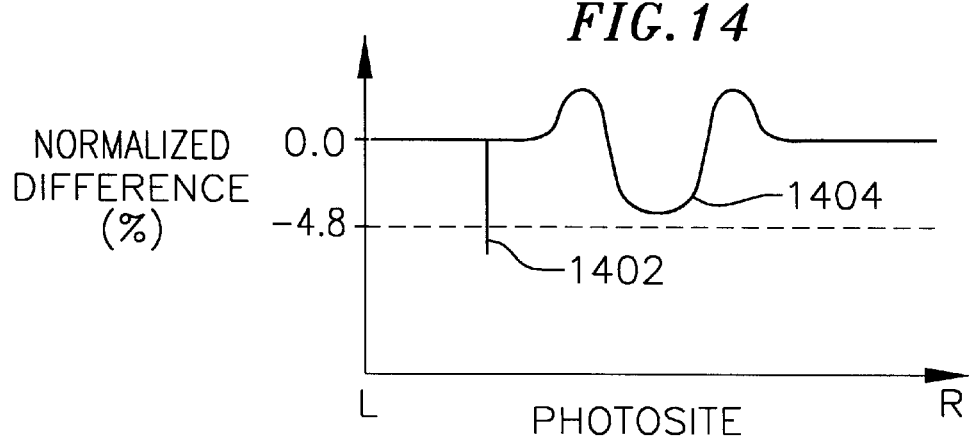
FIG. 14 is a graph showing normalized differences (ND) for the photosite output signal levels of FIG. 13 calculated according the method of FIGS. 11A–11C.

FIGS. 13 and 14 conceptually illustrate the processing of decisional diamond 1114. FIG. 13 shows the output signals 302 during calibration, from the left end 222 to the right end 224 of the optical sensor device 202. A deep, narrow dip 1302 and a shallow, wide dip 1304 caused by optical obstructions are shown in the figure. FIG. 14 shows the normalized differences (ND) for the output signals 302 of FIG. 13. The "normalized difference domain" plot of FIG. 14 includes a deep, narrow dip 1402 and a shallow, wide dip 1404 which correspond to the deep, narrow dip 1302 and the shallow, wide dip 1304, respectively. Proportionate gain is applied at executable block 1120 to the pixels of the shallow, wide dip 1304 because none of their respective NDs is less than −4.8%. However, since the ND is less than −4.8% for the pixel(s) of the deep, narrow dip 1302, the processing, to determine what type of gain should be applied to these pixel(s) continues, advancing to step 1116. It should be understood that the magnitude of the −4.8% threshold can vary from one application to another and is merely an appropriate threshold for the exemplary preferred embodiment disclosed herein. Furthermore, the polarity of the threshold can vary depending upon how the normalized difference is defined.

The exemplary preferred method 1100 also distinguishes between optical obstructions which are reflective and those which are light-absorbing. The ability to make this distinction provides additional flexibility in determining what type of gain should be applied to pixels. Reflective optical obstructions typically comprise small pieces of glass and silver which remain in the optical path 220 as a result of the scanner manufacturing process. Since reflective optical obstructions usually are not found on the scan area surface 210 where it is possible for them to come into contact with an object 212 being scanned—for example, as the object 212 moves along the "slow scan" axis 240—proportionate gains are applied to pixels for which it is determined that reflective optical obstructions are affecting their output signals 302.

Referring to FIG. 11B, the decisional diamond 1116 involves determining whether the value of a pixel under consideration indicates that a reflective optical obstruction is in an optical path of the pixel. In an exemplary preferred embodiment of the present invention, the answer to this question is "yes" (reflective optical obstruction) if the pixel under consideration has a more positive value than its neighbor pixels. Proportionate gain is applied at executable block 1120 (FIG. 11C) to these pixels. If it is determined at decisional diamond 1116 that a reflective optical obstruction is not in an optical path of the pixel, then the processing continues to determine what type of gain should be applied to pixel.

Now that it has been determined that the pixel under consideration has a light-absorbing optical obstruction in its optical path, the next step of the process 1100 is to determine whether there is a substantial likelihood that the light-absorbing optical obstruction is positioned between the calibration strip 208 and the scan surface area 210.

It has been observed that deep, narrow dips in the output signal levels of the optical sensor 202 are often caused by light-absorbing optical obstructions which are positioned between the calibration strip 208 and the scan surface area 210. It has also been observed that wide, shallow dips in the output signal levels of the optical sensor 202 are often caused by light-absorbing optical obstructions which are not positioned between the calibration strip 208 and the scan surface area 210, but elsewhere in the optical path 220.

Referring to FIG. 11C, the decisional diamond 1118 distinguishes between pixels which are part of a deep, narrow dip and pixels which are part of a wide, shallow dip. In an exemplary preferred embodiment of the present invention, the pixel under consideration is determined to be part of a wide dip if more than 6 of the normalized differences (NDs) of its "20 nearest neighbors" are less than an empirically determined threshold, e.g., −4.0%. In an exemplary preferred embodiment of the present invention, the term "20 nearest neighbors" means the 10 nearest pixels in the left and right directions along the fast scan axis 230, including the pixels in the left and right groups of skipped pixels 1206, 1208. It should be understood that the definition of nearest neighbors, the number of nearest neighbor which must have a ND lower than the threshold and the value of the threshold itself can vary depending upon the particular application. Furthermore, other approaches to determining whether the pixel under consideration is part of a wide or narrow dip can be employed without departing from the scope of the present invention.

If the answer to the question posed in decisional diamond 118 is "yes", the processing advances to executable block 1120 where a proportionate gain is applied to the pixel under consideration. If the answer to this question is "no", the processing advances to executable block 1122 where a gain appropriate for neighbor pixels of the pixel under consideration is applied to the pixel under consideration. In an exemplary preferred step 1122, an average gain for the left and right groups 1202, 1204 of pixels is applied to the pixel under consideration. It should be understood, however, that the gain smoothing function of step 1122 can be implemented in consideration of the gains appropriate for different groups of neighbor pixels.

With respect to the pixels associated with the left and right edges 222, 224 of the optical sensor 202, values for non-existing adjacent pixels are extrapolated.

Although the present invention has been described in terms of the preferred embodiment above, numerous modifications and/or additions to the above-described preferred embodiment would be readily apparent to one skilled in the art. It is intended that the scope of the present invention extends to all such modifications and/or additions.

We claim:

1. A method for automatic prevention of vertical streaks, the method comprising the steps of:

during a calibration of an optical sensor, processing output signals from sensor elements of the optical sensor; and selectively applying gains to the output signals depending upon differences between each output signal and its respective neighbor output signals, excluding output signals from sensor elements adjacent the sensor element under consideration.

2. A method as claimed in claim 1, wherein the optical sensor comprises an array of photosites.

3. A method as claimed in claim 1, wherein the optical sensor is a color image sensor.

4. A method as claimed in claim 1, wherein the step of selectively applying gains includes:

identifying an output signal for which the difference between the output signal and its neighbor output signals indicates that an optical obstruction is not likely to be present in an optical path associated with the output signal; and applying a proportionate gain to the output signal.

5. A method as claimed in claim 4, wherein the identifying step includes:

determining a normalized difference between the output signal and its neighbor output signals.

6. A method as claimed in claim 1, wherein the step of selectively applying gains includes:
   identifying an output signal for which the difference between the output signal and its neighbor output signals indicates that a reflective particle is likely to be present in an optical path associated with the output signal; and
   applying a proportionate gain to the output signal.

7. A method as claimed in claim 1, wherein the step of selectively applying gains includes:
   identifying an output signal for which the difference between the output signal and its neighbor output signals indicates that an optical obstruction is likely to be positioned in an optical path associated with the output signal between the optical sensor and a scan area surface over which an object to be imaged by the optical sensor is positioned; and
   applying a proportionate gain to the output signal.

8. A method as claimed in claim 7, wherein the identifying step includes:
   determining a normalized difference between the output signal and its neighbor output signals.

9. A method as claimed in claim 1, wherein the step of selectively applying gains includes:
   identifying an output signal for which the difference between the output signal and its neighbor output signals indicates that an optical obstruction is likely to be positioned in an optical path associated with the output signal on or between a scan surface area over which an object to be imaged by the optical sensor is positioned and a calibration strip facing the scan area surface; and
   applying a gain to the output signal, the gain being determined from a gain which is appropriate for at least one of the neighbor output signals.

10. A method as claimed in claim 9, wherein the identifying step includes:
    determining a normalized difference between the output signal and its neighbor output signals.

11. A method for automatic prevention of vertical streaks, the method comprising the steps of:
    during a calibration of a plurality of optical sensor elements, receiving output signals from the optical sensor elements; and
    for each of the sensor elements, comparing the value of the output signal with the values of the output signals of neighbor sensor elements to determine whether an optical obstruction appears to be present in an optical path associated with any of the sensor elements.

12. A method as claimed in claim 11, wherein the optical sensor elements are configured in an array.

13. A method as claimed in claim 11, wherein the optical sensor elements are adapted to sense different colors.

14. A method as claimed in claim 12, further comprising the steps of:
    distinguishing between narrow dips and wide dips in magnitudes of the output signals moving linearly across the array; and
    applying gains to the output signals depending upon whether the dips are narrow or wide.

15. A method as claimed in claim 14, wherein a proportionate gain is applied to output signals associated with the wide dips.

16. A method as claimed in claim 14, wherein a gain determined from gains appropriate for neighbor output signals is applied to output signals associated with the narrow dips.

17. A method as claimed in claim 12, further comprising the step of:
    determining whether changes in the output signals, moving spatially across the array, are greater for a sensor element than for its neighbor sensor elements.

18. A method for automatic prevention of vertical streaks, the method comprising the steps of:
    processing output signals from an optical sensor; and
    selectively applying gains to the output signals depending upon differences between each output signal and its respective neighbor output signals;
    wherein the step of selectively applying gains includes
        identifying an output signal for which the difference between the output signal and its neighbor output signals indicates that an optical obstruction is not likely to be present in an optical path associated with the output signal, and
        applying a proportionate gain to the output signal;
    wherein the identifying step includes
        determining a normalized difference between the output signal and its neighbor output signals.

19. A method for automatic prevention of vertical streaks, the method comprising the steps of:
    processing output signals from an optical sensor; and
    selectively applying gains to the output signals depending upon differences between each output signal and its respective neighbor output signals;
    wherein the step of selectively applying gains includes
        identifying an output signal for which the difference between the output signal and its neighbor output signals indicates that an optical obstruction is likely to be positioned in an optical path associated with the output signal between the optical sensor and a scan area surface over which an object to be imaged by the optical sensor is positioned, and
        applying a proportionate gain to the output signal;
    wherein the identifying step includes
        determining a normalized difference between the output signal and its neighbor output signals.

20. A method for automatic prevention of vertical streaks, the method comprising the steps of:
    processing output signals from an optical sensor; and
    selectively applying gains to the output signals depending upon differences between each output signal and its respective neighbor output signals;
    wherein the step of selectively applying gains includes
        identifying an output signal for which the difference between the output signal and its neighbor output signals indicates that an optical obstruction is likely to be positioned in an optical path associated with the output signal on or between a scan surface area over which an object to be imaged by the optical sensor is positioned and a calibration strip facing the scan area surface, and
        applying a gain to the output signal, the gain being determined from a gain which is appropriate for at least one of the neighbor output signals;
    wherein the identifying step includes
        determining a normalized difference between the output signal and its neighbor output signals.

21. A method for automatic prevention of vertical streaks, the method comprising the steps of:
    receiving output signals from a plurality of optical sensor elements configured in an array;
    for each of the sensor elements, comparing the value of the output signal with the values of the output signals of neighbor sensor elements to determine whether an optical obstruction appears to be present in an optical path associated with any of the sensor elements;

distinguishing between narrow dips and wide dips in magnitudes of the output signals moving linearly across the array; and applying gains to the output signals depending upon whether the dips are narrow or wide.

22. A method as claimed in claim 21, wherein a proportionate gain is applied to output signals associated with the wide dips.

23. A method as claimed in claim 21, wherein a gain determined from gains appropriate for neighbor output signals is applied to output signals associated with the narrow dips.

24. A method for automatic prevention of vertical streaks, the method comprising the steps of:

receiving output signals from a plurality of optical sensor elements configured in an array;

for each of the sensor elements, comparing the value of the output signal with the values of the output signals of neighbor sensor elements to determine whether an optical obstruction appears to be present in an optical path associated with any of the sensor elements; and determining whether changes in the output signals, moving spatially across the array, are greater for a sensor element than for its neighbor sensor elements.

* * * * *